US007275542B2

(12) United States Patent
Lurie et al.

(10) Patent No.: US 7,275,542 B2
(45) Date of Patent: *Oct. 2, 2007

(54) BAG-VALVE RESUSCITATION FOR TREATMENT OF HYPOTENSION, HEAD TRAUMA, AND CARDIAC ARREST

(75) Inventors: Keith Lurie, Minneapolis, MN (US); Vern Menk, Minneapolis, MN (US); Todd Zielinski, Minneapolis, MN (US); James W. Biondi, North Haven, CT (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/127,993

(22) Filed: May 11, 2005

(65) Prior Publication Data

US 2005/0217677 A1    Oct. 6, 2005

Related U.S. Application Data

(63) Continuation of application No. 10/660,366, filed on Sep. 11, 2003, now Pat. No. 6,938,618.

(51) Int. Cl.
*A61M 16/00* (2006.01)
(52) U.S. Cl. .................. 128/205.24; 128/203.11; 128/204.23; 128/204.28
(58) Field of Classification Search .......... 128/203.11, 128/203.15–203.17, 202.28, 202.29, 204.18, 128/204.21, 204.26, 204.28, 205.13–205.19, 128/205.24, 205.25, 207.12, 207.14, 205.2
See application file for complete search history.

(56) References Cited

U.S. PATENT DOCUMENTS

| 2,774,346 A | 12/1956 | Halliburton |
| 3,077,884 A | 2/1963 | Batrow et al. |
| 3,191,596 A | 6/1965 | Bird et al. |
| 3,307,541 A | 3/1967 | Hewson |
| 3,459,216 A | 8/1969 | Bloom et al. |
| 3,515,163 A | 6/1970 | Freeman |

(Continued)

FOREIGN PATENT DOCUMENTS

CA    668771    8/1963

(Continued)

OTHER PUBLICATIONS

Christenson, J.M., "Abdominal Compressions During CPR: Hemodynamic Effects of Altering Timing and Force", The Journal of Emergency Medicine, vol. 10, pp. 257-266, 1992.

(Continued)

*Primary Examiner*—Justine R. Yu
*Assistant Examiner*—Shumaya B. Ali
(74) *Attorney, Agent, or Firm*—Townsend and Townsend and Crew LLP (57) ABSTRACT

A device for manipulating intrathoracic pressures comprises a compressible bag structure, and an interface member coupled to the bag structure. A one way forward valve is coupled to the bag structure to permit respiratory gas to flow to the patient when the bag structure is compressed. A one way exit valve is employed to allow respiratory gases to be pulled from the person's airway upon decompression of the bag structure to produce a negative intrathoracic pressure.

21 Claims, 4 Drawing Sheets

U.S. PATENT DOCUMENTS

| | | | |
|---|---|---|---|
| 3,662,751 | A | 5/1972 | Barkalow et al. |
| 3,669,108 | A | 6/1972 | Sundblom et al. |
| 3,794,043 | A | 2/1974 | McGinnis |
| 3,815,606 | A | 6/1974 | Mazal |
| 3,834,383 | A | 9/1974 | Weigl et al. |
| 3,933,171 | A | 1/1976 | Hay |
| 4,041,943 | A | 8/1977 | Miller |
| 4,077,404 | A | 3/1978 | Elam |
| 4,166,458 | A | 9/1979 | Harrigan |
| 4,226,233 | A | 10/1980 | Kritzer |
| 4,259,951 | A | 4/1981 | Chernack et al. |
| 4,298,023 | A | 11/1981 | McGinnis |
| 4,316,458 | A | 2/1982 | Hammerton-Fraser |
| 4,320,754 | A | 3/1982 | Watson et al. |
| 4,349,015 | A | 9/1982 | Alferness |
| 4,397,306 | A | 8/1983 | Weisfeldt et al. |
| 4,446,864 | A | 5/1984 | Watson et al. |
| 4,449,526 | A | 5/1984 | Elam |
| 4,481,938 | A | 11/1984 | Lindley |
| 4,533,137 | A | 8/1985 | Sonne |
| 4,601,465 | A | 7/1986 | Roy |
| 4,809,683 | A | 3/1989 | Hanson |
| 4,827,935 | A | 5/1989 | Geddes et al. |
| 4,881,527 | A | 11/1989 | Lerman |
| 4,898,166 | A | 2/1990 | Rose et al. |
| 4,928,674 | A | 5/1990 | Halperin et al. |
| 5,014,698 | A | 5/1991 | Cohen |
| 5,016,627 | A | 5/1991 | Dahrendorf |
| 5,050,593 | A | 9/1991 | Poon |
| 5,056,505 | A | 10/1991 | Warwick et al. |
| 5,109,840 | A | 5/1992 | Daleidon |
| 5,163,424 | A | 11/1992 | Kohnke |
| 5,184,620 | A | 2/1993 | Cudahy et al. |
| 5,193,544 | A | 3/1993 | Jaffe |
| 5,217,006 | A | 6/1993 | McCulloch |
| 5,235,970 | A | 8/1993 | Augustine |
| 5,263,476 | A | 11/1993 | Henson |
| 5,295,481 | A | 3/1994 | Geeham |
| 5,301,667 | A | 4/1994 | McGrail et al. |
| 5,305,743 | A | 4/1994 | Brain |
| 5,355,879 | A | 10/1994 | Brain |
| 5,359,998 | A | 11/1994 | Lloyd |
| 5,377,671 | A | 1/1995 | Biondi et al. |
| 5,392,774 | A | 2/1995 | Sato |
| 5,398,714 | A | 3/1995 | Price |
| 5,454,779 | A | 10/1995 | Lurie et al. |
| 5,492,116 | A | 2/1996 | Scarberry et al. |
| 5,496,257 | A | 3/1996 | Kelly |
| 5,517,986 | A | 5/1996 | Starr et al. |
| 5,551,420 | A | 9/1996 | Lurie et al. |
| 5,628,305 | A | 5/1997 | Melker |
| 5,632,298 | A | 5/1997 | Artinian |
| 5,645,522 | A | 7/1997 | Lurie et al. |
| 5,692,498 | A * | 12/1997 | Lurie et al. ............ 128/205.24 |
| 5,697,364 | A * | 12/1997 | Chua et al. ............ 128/204.21 |
| 5,704,346 | A | 1/1998 | Inoue |
| 5,730,122 | A | 3/1998 | Lurie |
| 5,735,876 | A | 4/1998 | Kroll et al. |
| 5,738,637 | A | 4/1998 | Kelly et al. |
| 5,782,883 | A | 7/1998 | Kroll et al. |
| 5,814,086 | A | 9/1998 | Hirschberg et al. |
| 6,029,667 | A | 2/2000 | Lurie |
| 6,062,219 | A | 5/2000 | Lurie et al. |
| 6,155,257 | A | 12/2000 | Lurie et al. |
| 6,224,562 | B1 * | 5/2001 | Lurie et al. .................. 601/41 |
| 6,234,985 | B1 * | 5/2001 | Lurie et al. .................. 601/41 |
| 6,312,399 | B1 * | 11/2001 | Lurie et al. .................. 601/41 |
| 6,425,393 | B1 | 7/2002 | Lurie et al. |
| 6,459,933 | B1 | 10/2002 | Lurie et al. |
| 6,463,327 | B1 | 10/2002 | Lurie et al. |
| 6,526,973 | B1 | 3/2003 | Lurie et al. |
| 6,536,432 | B2 * | 3/2003 | Truschel ................ 128/205.23 |
| 6,578,574 | B1 | 6/2003 | Kohnke |
| 6,587,726 | B2 | 7/2003 | Lurie et al. |
| 6,604,523 | B2 | 8/2003 | Lurie et al. |
| 6,792,947 | B1 | 9/2004 | Bowden |
| 6,938,618 | B2 * | 9/2005 | Lurie et al. ............ 128/205.24 |
| 6,986,349 | B2 * | 1/2006 | Lurie .................... 128/202.28 |
| 7,032,596 | B2 * | 4/2006 | Thompson et al. ..... 128/205.13 |
| 7,082,945 | B2 * | 8/2006 | Lurie .................... 128/205.24 |
| 2001/0029339 | A1 | 10/2001 | Orr et al. |
| 2002/0069878 | A1 | 6/2002 | Lurie et al. |
| 2002/0170562 | A1 * | 11/2002 | Lurie et al. ............ 128/205.24 |
| 2003/0037764 | A1 | 2/2003 | Lurie |
| 2003/0062041 | A1 | 4/2003 | Lurie et al. |
| 2004/0200474 | A1 * | 10/2004 | Lurie .................... 128/203.11 |
| 2004/0211416 | A1 * | 10/2004 | Lurie .................... 128/203.11 |
| 2004/0231664 | A1 * | 11/2004 | Lurie et al. ............ 128/200.11 |
| 2005/0165334 | A1 * | 7/2005 | Lurie ......................... 601/44 |

FOREIGN PATENT DOCUMENTS

| | | |
|---|---|---|
| CA | 2077608 A1 | 3/1993 |
| DE | 24 53 490 A1 | 5/1975 |
| EP | 0 029 352 A1 | 5/1981 |
| EP | 0 139 363 A1 | 5/1985 |
| EP | 0 245 142 A1 | 11/1987 |
| EP | 0 367 285 B1 | 5/1990 |
| EP | 0 411 714 A1 | 2/1991 |
| EP | 0 509 773 A1 | 10/1992 |
| GB | 1 465 127 | 2/1977 |
| GB | 2 139 099 A | 11/1984 |
| WO | WO90/05518 A1 | 5/1990 |
| WO | WO93/21982 A1 | 11/1993 |
| WO | WO94/26229 A1 | 11/1994 |
| WO | WO95/13108 A1 | 5/1995 |
| WO | WO95/28193 A1 | 10/1995 |
| WO | WO96/28215 A1 | 9/1996 |
| WO | WO99/63926 A1 | 12/1999 |
| WO | WO01/70332 A1 | 9/2001 |
| WO | WO02/092169 A1 | 11/2002 |

OTHER PUBLICATIONS

Cohen, Todd J. et al., "Active Compression-Decompression Resuscitation: a Novel Method of Cardiopulmonary Resuscitation", Department of Medicine and the Cardiovascular Research Institute, UC San Francisco, American Heart Journal, 126(5):1145-1150, 1992.

Cohen, Todd J. et al., "Active Compression-Decompression: A New Method of Cardiopulmonary Resuscitation", JAMA 267(21):2916-2923 (Jun. 3, 1992).

Ambu International A/S "Directions for use of Ambu® CardioPump™", 8 pages.

Dupuis, Yvon G., *Ventilators-Theory and Clinical Application*, pp. 447-448, 481, 496; Jan. 1986, Mosby Compnay.

Geddes, L.A. et al., "Inspiration Produced by Bilateral Electromagnetic, Cervical Phrenic Nerve Stimulation In Man," IEEE Transactions on Biomedical Engineering 38(9): 1047-1048 (Oct. 1991).

Geddes, L.A. et al., "Optimum Stimulus Frequency for Contracting the Inspiratory Muscles with chest Surface Electrodes to Produce Artificial respiration," Annals of Biomedical Engineering 18:103-108 (1990).

Geddes, L.A., "Eletrically Produced Artificial Ventilation," Medical Instrumentation 22(5): 263-271 (1988).

Geddes, L.A., "Electroventilation—A Missed Opportunity?", Biomedical Instrumentation & Technology, Jul./Aug. 1998, pp. 401-414.

Glenn, William W.L. et al., "Diaphragm Pacing by Electrical Stimulation of the Phrenic Nerve," Neurosurgery 17(6): 974-984 (1985).

Glenn, William W.L., et al., "Twenty Years of Experience in Phrenic Nerve Stimulation to Pace the Diaphragm," Pace 9: 780-784 (Nov./Dec. 1986, Part I).

Kotze, P.L. et al., "Diaphragm Pacing in the Treatment of Ventilatory Failure," San. Deel 68:223-224.

Laghi, Franco et al., "Comparison of Magnetic and Electrical Phrenic Nerve Stimulation in assessment of Diaphragmantic Contractility," American Physiological society, pp. 1731-1742 (1996).

Lindner, Karl H. et al., "Effects of Active Compression-Decompression Resuscitation on Myocardial and Cerebral Blood Flow in Pigs" Department of Anesthesiology and Critical Care Medicine, University of Ulm, Germany, Circulation 88(3):1254-1263, (Oct. 7, 1993).

Lurle, Keith G. et al., "Regulated to Death: The Matter of Informed Consent for Human Experimentation In Emergency Resuscitation Research," Cardiac Arrhythmia Center at the University of Minnesota, PACE 18:1443-1447 (Jul. 1995).

Mushin W. W. et al., "Automatic Ventilation of the Lungs—The Lewis-Leigh Inflating Valve," Blackwell Scientific, Oxford, GB, p. 838.

US 5,584,866, 12/1996, Kroll et al. (withdrawn)

* cited by examiner

BAG-VALVE RESUSCITATION FOR TREATMENT OF HYPOTENSION, HEAD TRAUMA, AND CARDIAC ARREST

CROSS-REFERENCES TO RELATED APPLICATIONS

This application is related to U.S. application Ser. No. 10/660,462, filed on the same date as the present application, entitled "Ventilator and Methods for Treating Head Trauma, the complete disclosure of which is herein incorporated by reference.

BACKGROUND OF THE INVENTION

This invention relates generally to the field of blood flow, and in particular to the optimization of blood flow to the heart and brain in states of low blood pressure, head trauma and cardiac arrest. In one aspect, the invention relates to the intentional manipulation of intrathoracic pressures to facilitate such blood flow.

Inadequate blood flow can have serious consequences and may result from a variety of conditions. For example, those suffering from low blood pressure may have inadequate blood flow to the heart and brain. This is especially true when low blood pressure is the result of blood loss, such as from a serious wound.

Head trauma is generally regarded as the leading cause of morbidity and mortality in the United States for children and young adults. Head trauma often results in swelling of the brain. Because the skull cannot expand, the increased pressures within the brain can lead to death or serious brain injury. While a number of therapies have been evaluated in order to reduce brain swelling, including use of hyperventilation and steroids, an effective way to treat intracranial pressures remains an important medical challenge. As described in copending U.S. application Ser. No. (Attorney Docket No. 16354-005211), filed on the same date as the present application, the effects of head trauma may be addressed by decreasing intracranial pressure and increasing cerebral cerebral spinal fluid flow and, to a lesser extent, increasing blood flow to the brain. The complete disclosure of this application is herein incorporated by reference.

Those suffering from cardiac arrest lose essentially all blood flow. If not promptly restored, the loss of blood flow can lead to brain injury or death, among other ailments

BRIEF SUMMARY OF THE INVENTION

In one embodiment, the invention provides a method for enhancing venous return to the heart. Such a method may be particularly useful for those suffering from cardiac arrest or low blood pressure where venous return to the heart is critical so that the returned blood may be re-oxygenated and circulated back through the body. The method may also be useful for those suffering from head trauma. In such cases, the decreased intrathoracic pressures cause a reduction in intracranial pressure, an increase in cerebral spinal fluid flow, and to a lesser extent an increase in blood flow to the brain. Together, this results in decreased brain pressures and secondary brain injury. According to the method, a positive pressure breath is delivered to a person. Respiratory gases are extracted from the person's airway following the positive pressure breath to create an intrathoracic vacuum to enhance venous return to the heart. The steps of delivering positive pressure breaths and extracting respiratory gases may be repeated to continue the treatment. In some embodiments, the timing of the positive pressure ventilation and generation of an vacuum to actively remove respiratory gases from the thorax and thereby decrease intracranial pressures and enhance venous return to the heart may be timed with the contraction and/or relaxation of the heart.

In some cases, such as when the person is breathing or during CPR, an impedance threshold valve may also be coupled to the person's airway. The threshold valve prevents airflow to the person's lungs when attempting to inspire until the threshold valve opens, thereby augmenting blood flow back to the heart. The threshold valve may be configured to open when the negative intrathoracic pressure exceeds about −6 cmH2O.

In another aspect, a flow limiting valve may be interfaced to the patient's airway to regulate the pressure and/or flow rate of the positive pressure breath. In a further aspect, a pressure source and a vacuum source may be interfaced to the person's airway to deliver the positive pressure breath and to extract the respiratory gases. Conveniently, the pressure source and the vacuum source may comprise a compressible bag system. In one aspect, the compressible bag system may be reconfigured to operate only as a pressure source. For example, the bag system may have a switch that is operated to place the bag system in a ventilate-only mode.

Another feature of the method is that the extracted respiratory gases may be exhausted to the atmosphere. In this way, the extracted air is not re-circulated to the person. In one aspect, the duration or amplitude of the positive pressure breaths or the extraction of the respiratory gases may be varied over time. If needed, the person may also be supplied with supplemental oxygen. Also, at least one physiological parameter of the person may be monitored, and the positive pressure breath or the extraction of respiratory gases may be varied based on the monitored parameter. Examples of physiological parameters include end tidal CO2, oxygen saturation, blood pressure, cardiac output and the like. Information on the measured parameter may be transmitted to a remote receiver In one particular aspect, the respiratory gases may be extracted upon recoiling of the compressible bag system. The volume of the positive pressure breath may also be measured.

In a further aspect, the intrathoracic vacuum lowers the person's intrathoracic pressure to about −1 mm Hg to about −20 mm Hg. This may be done using an intrathoracic vacuum in the range from about −2 mm Hg to about −60 mm Hg.

The invention also provides a method for treating a person suffering from cardiac arrest. According to the method, a person's chest is repeatedly compressed. Respiratory gases are prevented or impeded from flowing to the person's lungs for at least some time between chest compressions. Periodically, a positive pressure breath is delivered to the person. Respiratory gases are extracted from the person's airway following the positive pressure breath to create an intrathoracic vacuum to enhance venous return to the heart. If needed, an impedance threshold valve may be coupled to the person's airway to prevent or impede the flow of respiratory gases.

The invention also provides a device for manipulating intrathoracic pressures. The device comprises a compressible bag structure, and an interface member that is coupled to the bag structure for interfacing with a person's airway. A one way forward valve is coupled to the bag structure to permit respiratory gases to flow to the person's airway upon compression of the bag structure. Also, a one way exit valve is coupled to the bag structure to permit respiratory gases to be pulled from the person's airway upon decompression of the bag structure, thereby producing a negative intrathoracic pressure.

The forward valve and the exit valve may take a variety of forms, such as a spring loaded check valve, a fish mouth valve, a ball valve, a disc valve, a baffle, a magnetic valve, an electronic valve, and the like. In one aspect, the bag structure is configured to produce a vacuum in the range from about −2 mm Hg to about −60 mm Hg to produce a negative intrathoracic pressure in the range from about −1 mm Hg to about −20 mm Hg.

Optionally, an impedance threshold valve may be coupled to the compressible bag structure. The threshold valve is configured to permit respiratory gases to flow to the person's lungs once a certain negative intrathoracic pressure is exceeded. In another aspect, a flow limiting valve may be coupled to the compressible bag to regulate the flow of respiratory gases to the patient's lungs upon compression of the bag structure. Optionally, a switch may be provided for permanently closing the exit valve.

In a further aspect, an exhaust valve may be coupled to the bag structure to permit respiratory gases pulled from the person's airway to be exhausted to the atmosphere. Also, an oxygen source may be used to provide supplemental oxygen to the person through the interface member. Further, at least one physiological sensor may be operably coupled to the compressible bag structure to measure at least one physiological parameter of the person. A transmitter may be coupled to the sensor to transmit information on the measured parameter to a remote receiver.

In one aspect, a regulation valve may be coupled to the bag structure to regulate the rate of flow of respiratory gases to the person's airway and/or the pressure of the respiratory gases delivered to the person's airway. In a further aspect, the bag structure may comprise a ventilation chamber that supplies respiratory gases through the forward valve upon compression of the bag structure and an expiration chamber that receives respiratory gases from the person through the exit valve upon decompression of the bag structure. Also, the bag structure may further comprise a venturi system that pulls respiratory gases from the person's lungs upon decompression of the bag structure. The bag structure may also constructed of an elastomeric or other spring-like material to permit it to decompress.

DETAILED DESCRIPTION OF THE INVENTION

The invention may be useful in optimizing blood flow to the heart and brain in states of low blood pressure, head trauma, cardiac arrest and the like. For those suffering from head trauma, venous return to the chest may reduce intracranial pressures as described in co-pending U.S. application Ser. No. 10/660,462, filed on the same date as the present application, the complete disclosure of which is herein incorporated by reference.

For those with low blood pressure, the increased circulation may help to increase their blood pressure. For those in cardiac arrest, blood circulation created by the invention serves to help maintain vital organ functions until resuscitation.

In order to provide such circulation, the invention may utilize any device capable of delivering a positive pressure breath followed by the creation of a vacuum to lower the person's intrathoracic pressure. This may be performed with a mechanical ventilator, a ventilation bag and the like.

One embodiment utilizes a ventilator bag that may be compressed and then released to deliver and then extract air from the person. Such a bag may include a valve system that permits a positive pressure breath to be delivered when compressing the bag (referred to as the inspiratory phase) and then immediately pull a vacuum as the bag is released to cause the pressure within the chest to fall less than atmospheric pressure during the expiratory phase.

In some cases, the bag may include a threshold valve as described in U.S. Pat. Nos. 5,551,420; 5,692,498; 6,062,219; 5,730,122; 6,155,257; 6,234,916 and 6,224,562, and in U.S. patent application Ser. No. 10/224,263, filed on Aug. 19, 2002 ("Systems and Methods filed Mar. 28, 2003 ("Diabetes Treatment Systems and Methods", Ser. No. 09/966,945, filed Sep. 28, 2001 and Ser. No. 09/967,029, filed Sep. 28, 2001, the complete disclosures of which are herein incorporated by reference. This valve arrangement may be used to prevent air from entering the person if the pressure within the chest is mechanically manipulated to fall (such as during the decompression phase of manual CPR or ACD CPR) during the expiratory phase.

In some cases, the rescuer may switch the operation from a "push-pull" ventilator to one that delivers only positive pressure ventilation, such as is traditional with most ventilator bags (e.g., an AMBU bag).

One reason for pulling the vacuum during the expiratory phase is to lower the intrathoracic pressure within the chest after each positive pressure ventilation. This negative pressure is transferred to the right heart and lungs, drawing more venous blood back from the extra-thoracic vasculature, and may be used to treat low blood pressure, head trauma and cardiac arrest.

The device may be configured to be hand-held, light weight and portable. As the bag decompresses, it "recharges" itself so that more air is available during the next squeeze. Optionally, a foot peddle may be connected to help develop a greater or more sustained vacuum. It may also include a timing device to provide feedback to the rescuers on how often to ventilate the patient. It may further include a regulator to limit the amount of pressure that builds up with each positive pressure ventilation to prevent stomach insufflation. One example of such a regulator is the SMART BAG®, commercially available from Mediline.

Figure 1:
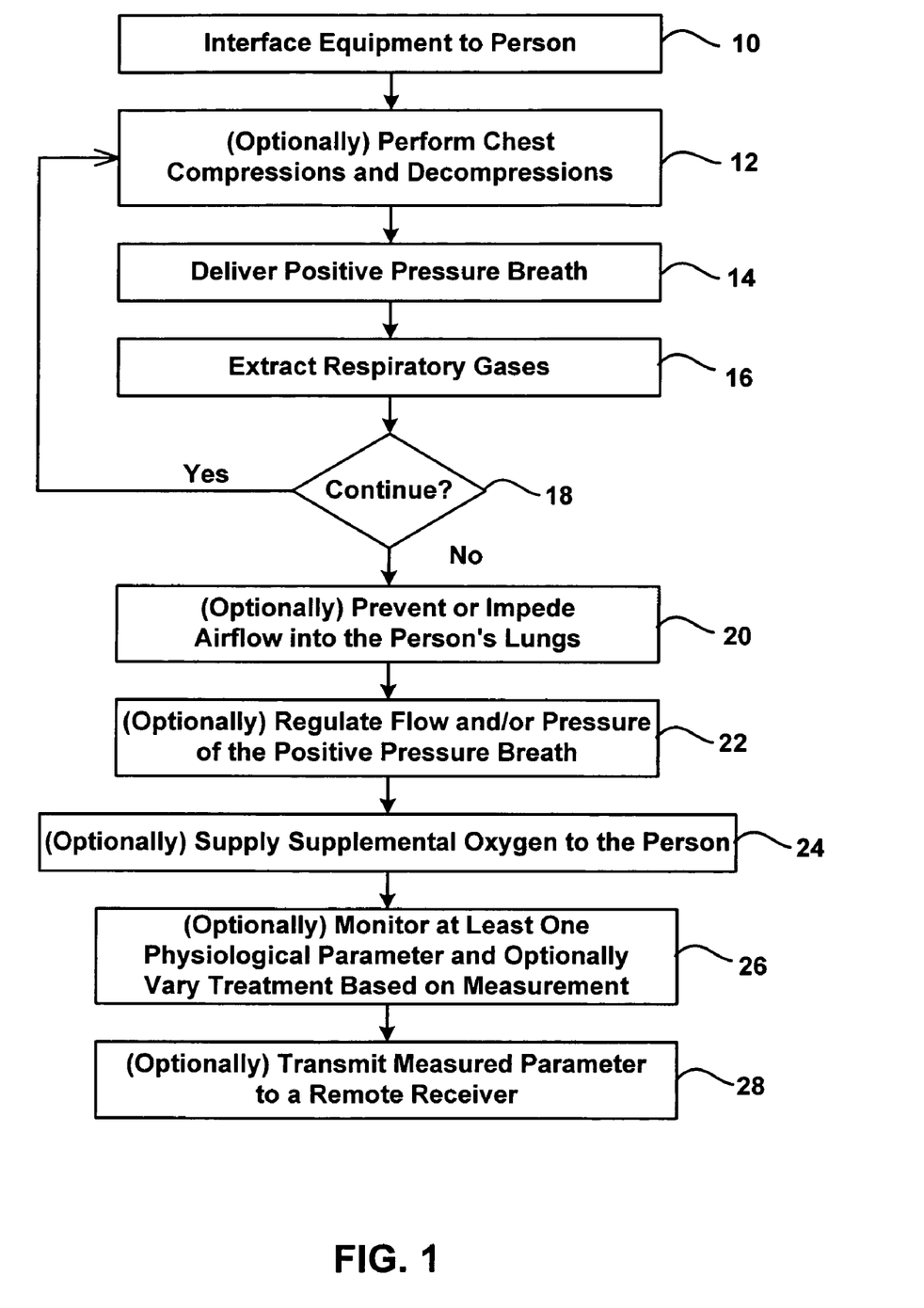
FIG. 1 is a flow chart illustrating one method for enhancing venous return to the heart according to the invention.

Referring now to FIG. 1, one method for enhancing blood circulation will be described. In so doing, it will be appreciated that such techniques may be used to treat those suffering from head trauma, low blood pressure, and cardiac arrest, among others.

At step 10, the process may begin by interfacing the appropriate equipment to the person. This may include, for example, a pressure and a vacuum source (such as a bag-valve system having a face mask), an impedance threshold valve, a positive pressure flow regulator, one or more physiological sensors, a transmitter for transmitting measured signals to a remote receiver, a metronome or other timing device to tell the rescuer when to ventilate and/or create a vacuum, an oxygen source and the like.

If the person is in cardiac arrest, the rescuer may perform CPR by performing chest compressions and decompressions as is known in the art. This is illustrated in step 12.

At step 14, a positive pressure breath is delivered to the person. This is immediately followed by the extraction of respiratory gases to lower the person's intrathoracic pressure as shown in step 16. Steps 12-16 may be repeated as necessary as shown in step 18. If the person is in cardiac arrest, the steps of delivering a breath and extracting respiratory gases are performed about once for every 5 to 20 chest compressions. The positive pressure breath may be delivered for about 0.5 to about 2.0 seconds while the vacuum may be produced for about 1 to about 10 seconds. The volume of air delivered may be in the range from about 4 ml/kg to about 20 ml/kg. The negative intrathoracic pressure created may be in the range from about −1 mmHg to about −20 mmHg. To create the pressure the generated vacuum may be about one to about three times this amount.

For those suffering from low blood pressure or head trauma, steps 14 and 16 may be continuously performed as long as treatment is needed. The positive pressure breath may last about 0.5 to about 3 seconds and have a volume of about 4 ml/kg to about 20 ml/kg. The vacuum may be produced immediately after the positive pressure breath and last about 1 second to a bout 6 seconds. The resulting negative intrathoracic pressure may be about −1 mm Hg to about −20 mm Hg and may be producing using a vacuum that is one to about three times this amount. Particular techniques for supplying the breath and extracting gases are described hereinafter with respect to FIGS. 5A-5C. Also, it will be appreciated that the vacuum may be producing using a flow of gases or with no flow, and the time and/or amount of the vacuum may be varied.

As shown in step 20, an impedance threshold valve or other device may be used to prevent or impede respiratory gases from entering the patient's lungs. This may be done, for example, when performing CPR. During decompression after the chest, air is typically drawn into the person's airway. Using an impedance valve, air is prevented from rushing in until a certain negative intrathoracic pressure is reached. At this time, the valve opens to permit gases to flow to the lungs. Such techniques are described in the references incorporated herein. For CPR applications, the valve may be set to open when the negative intrathoracic pressure exceeds about −4 cmH$_2$O to about −15 cmH$_2$O. Such an impedance valve may also be used in non-CPR applications as well when the person inspires. In such cases, the valve may be set to open at about −3 cm H$_2$O to about −12 cmH$_2$O.

In step 22, the volume, rate and or pressure of the positive pressure breath may be regulated. In this way, the patient may be protected against insufflation. In step 24, supplemental oxygen may be supplied to the patient. This may be supplied based on measured parameter as described below. Also, the oxygen may be delivered to the bag-valve system.

In step 26, one or more physiological parameters may optionally be monitored. The treatments described herein may be varied based on the measured parameters. Examples of such parameters include end tidal CO$_2$, oxygen saturation, blood pressure, cardiac output and the like. Other parameters as well as equipment and sensors that maybe be used are described in copending U.S. application Ser. No. 10/660,462, filed on the same date as the present application (and incorporated therein by reference) as well as in the other references incorporated herein. These may be coupled to a controller or other computer to record the measurements, display the measured parameters, recommend or control a specific treatment and the like.

As shown in step 28, information on the measured parameter may also be transmitted to a remote receiver. This may be over a variety of communication paths or networks, such as wireless networks, cell phones, local area networks, the Internet and the like. This information may be used to evaluate the treatment, monitor the quality of treatment, and command a treatment or the like. For example, the information may be transmitted to a hospital or health care facility where a physician may recommend how to apply the positive pressure breaths or extract the respiratory gases.

Figure 2:
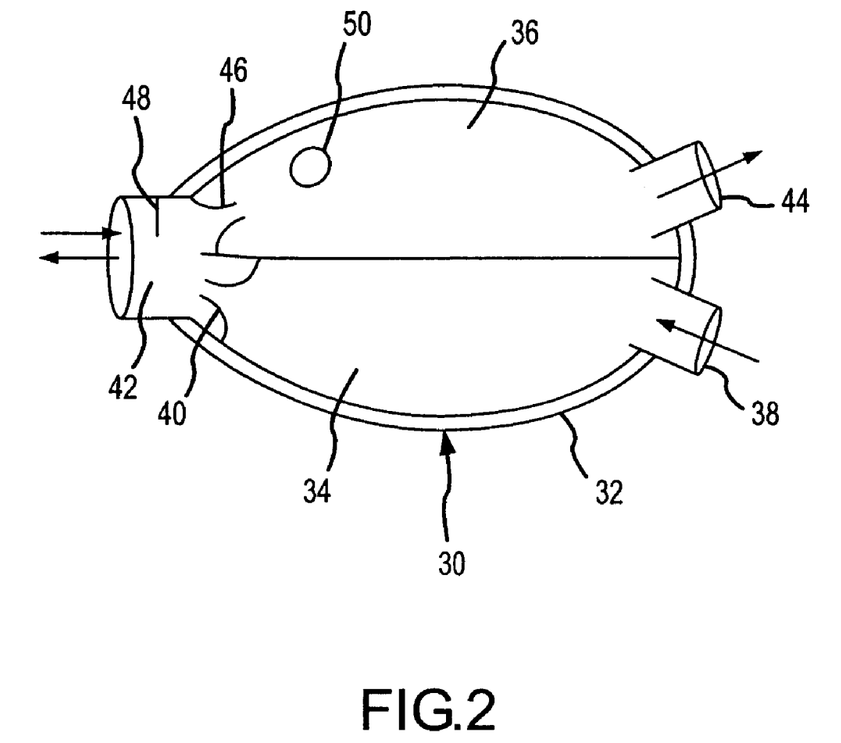
FIG. 2 is a schematic diagram of one embodiment of a bag-valve resuscitation system according to the invention.

Referring now to FIG. 2, one embodiment of a bag-valve resuscitator 30 will be described. Resuscitator 30 may be used in association with any of the methods described herein. Resuscitator 30 comprises a compressible bag 32 that is divided into a supply chamber 34 and an exit chamber 36. Bag 32 may be constructed of an elastomeric material that permits bag 32 to self-expand after it has been compressed. Optionally, an elastomeric material may be placed in one or both of the chambers to facilitate expansion of bag 32 after it has been compressed. Bag 32 also includes an entrance port 38 and a one-way inflow valve 40. When bag 32 is compressed, air, oxygen or other respiratory gases in supply chamber 34 are forced through inflow valve 40 and into a conduit 42 where they may be supplied to a person's airway. Optionally, an interface may be coupled to conduit 42 to couple resuscitator 30 to the patient. Such interfaces may include facial masks, endotracheal tubes, and the like. When bag 32 is released, it expands to its normal position. In so doing, inflow valve 40 closes allowing air or other respiratory gases to flow into chamber 34. Optionally, a flow restrictive device may be used to regulate the flow of air into conduit 42. This may provide a fixed resistance or a variable resistance.

Bag 32 also includes an exit port 44 and a one way outflow valve 46. When bag 32 is compressed, valve 46 closes and gases in chamber 36 may exit through port 44. As bag 32 expands, valve 46 opens to pull respiratory gases from the patient's airway. Hence, a positive pressure breath may be delivered when bag 32 is compressed and gases may be extracted when bag 32 is released. In so doing, the person's intrathoracic pressure is lowered to pull venous blood back into the chest.

Optionally, one or more sensors 48 may be incorporated into or coupled to resuscitator 30. Examples of sensors that may be used include any of those described or incorporated herein. As another option, a timer 50 may be coupled to or associated with bag 32. Timer 50 may be a flashing light, a speaker or the like to indicate when bag 32 should be compressed. This information may be pre-programmed or varied based upon measurements from sensor 48.

Figure 3:
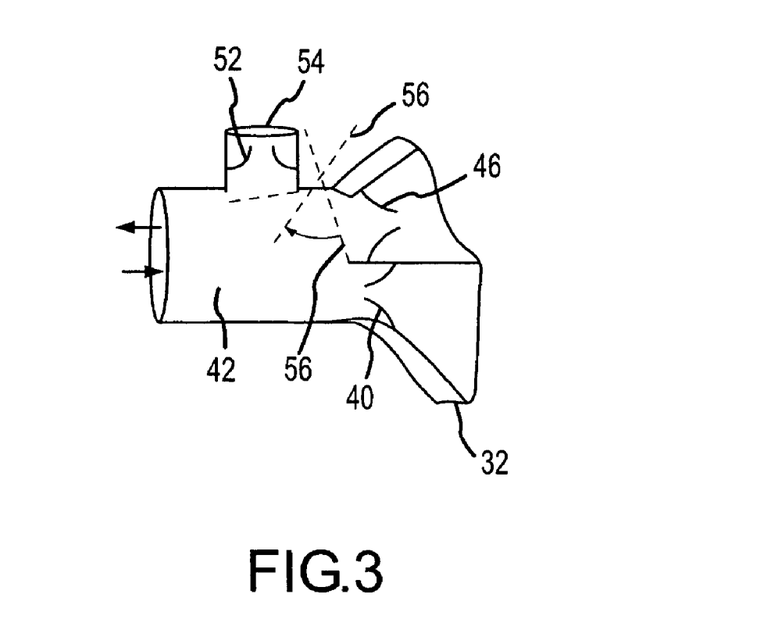
FIG. 3 illustrates a valve arrangement of the system of FIG. 2 along with a positive end expiratory pressure valve according to the invention.

As shown in FIG. 3, conduit 42 may be modified to include a positive end expiratory pressure (PEEP) valve 52 for non-breathing patients. This is located in a non-breather port 54. PEEP valve 52 may be used when the resuscitator bag is switched from one device capable of "pushing and pulling" to one that is locked in the "traditional" positive pressure ventilator mode only. However, in some cases, PEEP valve 52 may be used intermittently, such as every other or every third ventilation cycle.

Resuscitator 30 may also include a switch or a closure valve 56 that may move to a position that blocks outflow valve 46. In so doing, the "pull" feature is turned off so that respiratory gases are not actively extracted during the expiratory phase. In another position, valve 56 may be moved to a position closing non-breather port 54. This option allows for standard positive pressure ventilation and for push/pull ventilation.

As another option, an impedance threshold valve may be positioned over conduit 42 or anywhere between the bag and the patient. This valve is particularly useful when performing CPR. When bag 32 is compressed, gases flow through the threshold valve and to the patient to provide proper ventilation. When performing CPR respiratory gases exiting the patient during compression of the chest pass through the impedance valve and out valve 46. During decompression of the chest, gases are prevented from entering the patient's lungs because of the impedance valve. This valve opens when a certain negative intrathoracic pressure is achieved when opened gases may enter conduit 42 through valve 40. Such an impedance valve is described in the references incorporated herein.

Figure 4:
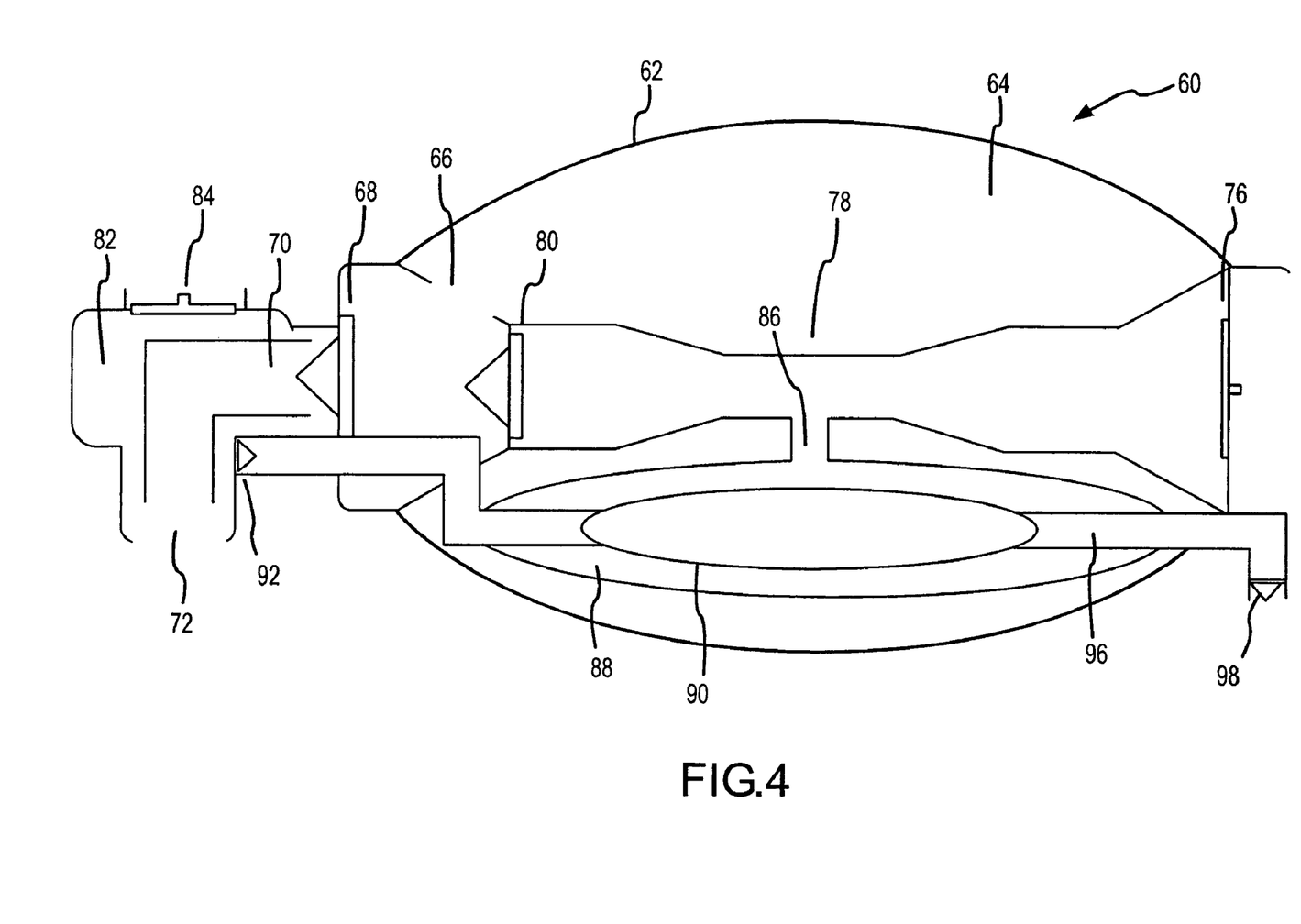
FIG. 4 is a schematic diagram of another embodiment of a bag-valve resuscitation system according to the invention.

FIG. 4 illustrates another embodiment of a bag-valve resuscitator 60 that comprises a compressible bag 62 that is constructed of an elastomeric material so that it will expand to its original shape following a compression. Bag 62 includes a main ventilation chamber 64 that is filled with air or other respiratory gases. When bag 62 is compressed, air in chamber 643 is directed through a ventilation port 66, through a fish mouth valve 68 and into a ventilation tube 70 where it is supplied to the patient through a patient support 72.

Ventilation chamber 64 is refilled as bag 62 is released and returns to its uncompressed shape. More specifically, as bag 62 decompresses, a negative pressure within main ventilation chamber 64 is produced. This opens a one way valve 76 allowing air to flow through a venturi tube 78, through a fish mouth valve 80, through ventilation port 66 and into chamber 64.

Following ventilation, passive expiratory gases from the patient may flow through patient port 72, into an expiratory chamber 82 and out a one way valve 84.

The generation of the negative intrathoracic pressure occurs during the passive recoil or decompression of bag 62. More specifically, air flowing through venturi tube 78 creates a venturi effect in tube 86. This creates a negative pressure within a negative chamber 88. In turn, this cases a secondary chamber 90 (which is collapsed) to pen, thereby including air flow through a fish mouth valve 92, through a supply tube 94 and into secondary chamber 90. Secondary chamber 90 may hold a volume of about 100 milliliters to about 150 milliliters when filled.

When bag 62 is again compressed, gas stored in secondary chamber 90 is directed through an exhaust tube 96 and expelled through a fish mouth valve 98.

Hence, resuscitator 60 may be used in any of the procedures described herein. Also, resuscitator 60 may include any of the other features described in connection with other embodiment described herein, such as flow regulators, threshold valve, sensors, PEEP valves, switches and the like.

Figure 5A:
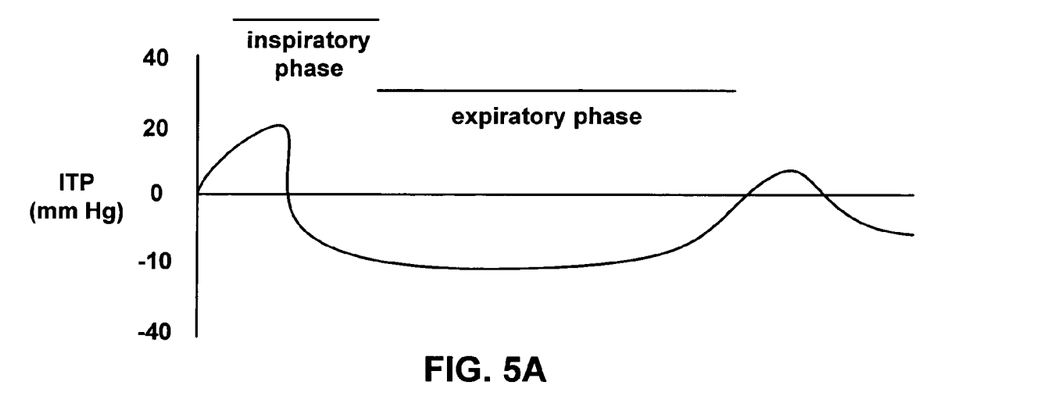
FIGS. 5A-5C show three graphics illustrating patterns for delivering a positive pressure breath and extracting respiratory gases according to the invention.
Figure 5B:
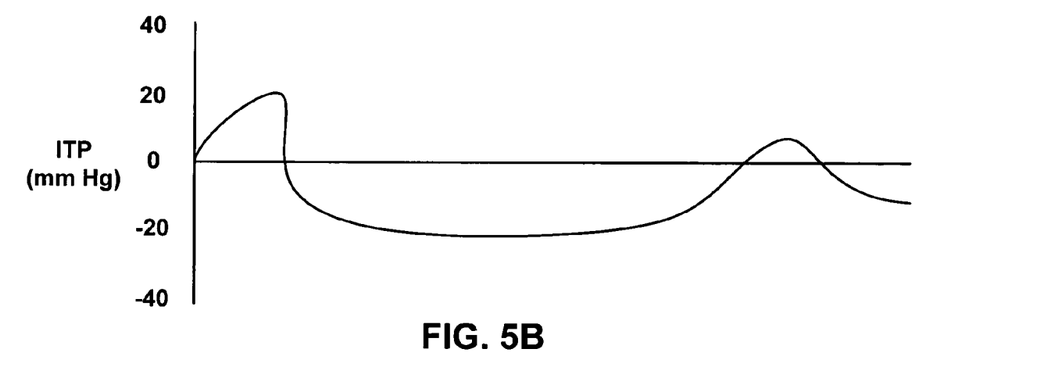
Figure 5C:
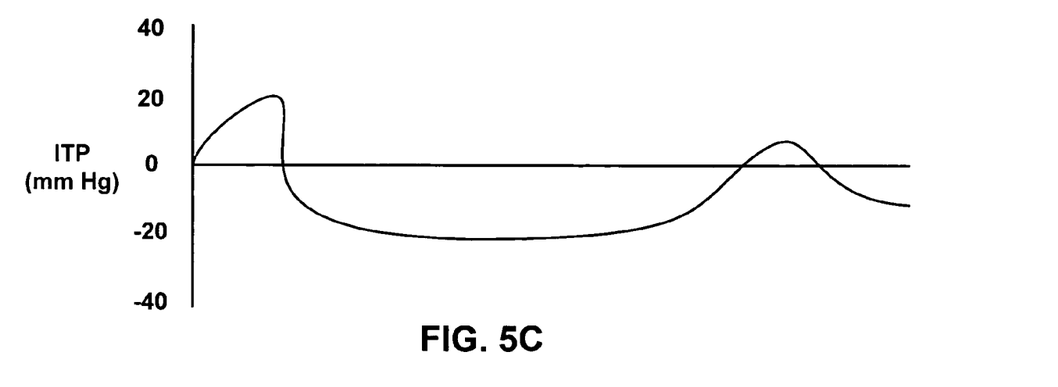

The manner in which positive pressure breaths and the vacuum are created may vary depending upon a particular application. These may be applied in a variety of waveforms having different durations and slopes. Examples include using a square wave, biphasic (where a vacuum is created followed by positive pressure, decay (where a vacuum is created and then permitted to decay), and the like. Three specific examples of how this may occur are illustrated in FIGS. 5A-5C, although others are possible. For convenience of discussion, the time during which the positive pressure breath occurs may be defined in terms of the inspiratory phase, and the time during which the intrathoracic pressure is lowered may be defined in terms of the expiratory phase. As shown in FIG. 5A, respiratory gases are quickly supplied up to a pressure of about 22 mmHg. This is immediately reversed to a negative pressure of about −10 mmHg. This pressure is kept relatively constant until the end of the expiratory phase where the cycle is repeated. In some cases, the cycle may go from a push-pull every breath to a push, then push-pull every other breath or every third breath, i.e. as a 2:1 or 3:1 push:pull option.

In FIG. 5B, the positive pressure is more slowly applied. When reaching a pressure of about 10 to about 15 mmHg, the pressure is rapidly reversed to a negative pressure of about −20 mmHg. The negative pressure gradually declines to about 0 mmHg at the end of the expiratory phase. The cycle is then repeated. Hence, in the cycle of FIG. 5B, the positive pressure is reduced compared to the cycle in FIG. 5A, and the negative pressure is initially lower, but allowed to gradually increase. The technique is designed to help reduce a possible airway collapse.

In FIG. 5C, the positive pressure is brought up to about 20 mmHg and then immediately brought down to about 0 mmHg. The negative pressure is then gradually increased to about −20 mmHg toward the end of the expiratory phase. This cycle is designed to help reduce a possible airway collapse.

The invention has now been described in detail for purposes of clarity and understanding. However, it will be appreciated that certain changes and modifications may be practiced within the scope of the appended claims.

What is claimed is:

1. A method for enhancing venous return to the heart, the method comprising:
   repetitively compressing and actively decompressing the patient's chest;
   providing artificial inspiration to a person suffering from low blood pressure or head trauma;
   using a vacuum source for actively extracting respiratory gases from the person's airway following the artificial inspiration to create an intrathoracic vacuum to enhance venous return to the heart, wherein the intrathoracic vacuum lowers the person's intrathoracic pressure to about −1 mm Hg to about −20 mm Hg; and
   repeating the steps of providing artificial inspiration and extracting respiratory gases.

2. A method as in claim 1, further comprising interfacing an impedance threshold valve to the person's airway, wherein the threshold valve prevents airflow to the person's lungs when attempting to inspire until the threshold valve opens, thereby augmenting blood flow back to the heart.

3. A method as in claim 2, wherein the threshold valve is configured to open when the negative intrathoracic pressure exceeds about −7 cm H2O.

4. A method as in claim 1, further comprising interfacing a flow limiting valve to the patient's airway and regulating the pressure or the volume of the artificial inspiration with the flow limiting valve.

5. A method as in claim 1, further comprising interfacing a pressure source and the vacuum source to the person to deliver the artificial inspiration and to extract the respiratory gases.

6. A method as in claim 5, wherein the pressure source and the vacuum source comprise a compressible bag system.

7. A method as in claim 6, further comprising reconfiguring the compressible bag system to operate only as a pressure source.

8. A method as in claim 6, wherein the respiratory gases are extracted upon recoiling of the compressible bag system.

9. A method as in claim 1, further comprising exhausting the extracted respiratory gases to the atmosphere.

10. A method as in claim 1, further comprising varying the duration of the artificial inspiration or the extraction of the respiratory gases over time.

11. A method as in claim 1, further comprising supplying supplemental oxygen to the person.

12. A method as in claim 1, further comprising monitoring at least one physiological parameter of the person and varying the artificial inspiration or the extraction of respiratory gases based on the monitored parameter.

13. A method as in claim 12, wherein the physiological parameters are selected from a group consisting of end tidal $CO_2$, oxygen saturation, intrathoracic pressure, blood pressure and cardiac output.

14. A method as in claim 12, further comprising varying the amplitude of the positive pressure breath or the rate of extraction of respiratory gases.

15. A method as in claim 12, further comprising transmitting information on the physiological parameter to a remote receiver.

16. A method as in claim 1, wherein the intrathoracic vacuum is in the range from about −2 mm Hg to about −60 mm Hg.

17. A method as in claim 1, further comprising measuring the volume of the artificial inspiration.

18. A method for treating a person with low blood circulation or low circulation to the brain who needs assisted ventilation, the method comprising:
   providing artificial inspiration for about 0.5 seconds to about 2 seconds to a person suffering from low blood pressure or head trauma;
   using a vacuum source for actively extracting breath to create an intrathoracic vacuum to enhance venous return to the heart wherein the intrathoracic vacuum lowers the person's intrathoracic pressure to about −1 mm Hg to about −20 mm Hg; and
   repeating the steps of delivering artificial inspiration and extracting respiratory gases.

19. A method for enhancing venous return to the heart, the method comprising:
   automatically providing artificial inspiration, as needed, for about 0.5 seconds to about 2 seconds to a person suffering from low blood pressure or head trauma;
   using a vacuum source for actively and actively extracting respiratory gases from the person's airway following the artificial inspiration to create an intrathoracic vacuum to enhance venous return to the heart, wherein the intrathoracic vacuum lowers the person's intrathoracic pressure to about −1 mm Hg to about −20 mm Hg; and
   repeating the steps of providing artificial inspiration and extracting respiratory gases.

20. A method for enhancing venous return to the heart, the method comprising:
   providing artificial inspiration for about 0.5 seconds to about 2 seconds to a person suffering from low blood pressure or head trauma;
   using a vacuum source to actively extract respiratory gases from the person's airway following the artificial inspiration to create an intrathoracic vacuum to enhance venous return to the heart, wherein the intrathoracic vacuum lowers the person's intrathoracic pressure to about −1 mm Hg to about −20 mm Hg; and
   repeating the steps of providing artificial inspiration and exacting respiratory gases.

21. A method for enhancing venous return to the heart, the method comprising:
   providing artificial inspiration for about 0.5 seconds to about 2 seconds to a person suffering from low blood pressure or head trauma;
   using a vacuum source for actively extracting respiratory gases form the person's airway following the artificial inspiration to create an intrathoracic vacuum to enhance venous return to the heart, wherein the intrathoracic vacuum lowers the person's intrathoracic pressure to about −1 mm Hg to about −20 mm Hg;
   repeating the steps of providing artificial inspiration and extracting respiratory gases; and
   using one or more physiological parameters to regulate the rate of extraction of respiratory gases from the person's airway following the artificial inspiration to create an intrathoracic vacuum to enhance venous return to the heart.

* * * * *